United States Patent [19]

Smith

[11] Patent Number: 5,324,318
[45] Date of Patent: Jun. 28, 1994

[54] COLD COMPRESS SYSTEM

[76] Inventor: Kirby Smith, P.O. Box 70425, Marietta, Ga. 30007

[21] Appl. No.: 545,295

[22] Filed: Jun. 28, 1990

Related U.S. Application Data

[60] Continuation of Ser. No. 408,761, Sep. 18, 1989, which is a continuation of Ser. No. 294,428, Jan. 9, 1989, abandoned, which is a division of Ser. No. 172,578, Mar. 24, 1988, abandoned.

[51] Int. Cl.$^5$ .............................................. A61F 7/00
[52] U.S. Cl. ................................... 607/104; 607/114; 607/111
[58] Field of Search ............... 128/384, 400, 402, 403, 128/DIG. 12, DIG. 27, DIG. 20, 898, 379, 82.1; 604/4; 606/142

[56] References Cited

U.S. PATENT DOCUMENTS

| | | | |
|---|---|---|---|
| 26,663 | 1/1860 | French | 128/400 |
| 267,435 | 11/1882 | Leiter . | |
| 500,568 | 7/1893 | Ells | 128/400 |
| 1,732,380 | 10/1929 | Sarason | 128/400 |
| 2,026,747 | 1/1936 | Nemzek | 128/400 |
| 2,832,336 | 4/1958 | Davis et al. | 128/402 |
| 2,930,594 | 3/1960 | MacCracken | 257/306 |
| 3,628,537 | 12/1971 | Berndt et al. | 128/400 |
| 3,683,902 | 8/1972 | Artememko | 128/400 |
| 3,717,145 | 2/1973 | Berndt et al. | 128/82.1 |
| 3,871,381 | 3/1975 | Roslonski | 128/402 |
| 3,888,259 | 6/1975 | Miley | 128/400 |
| 3,905,367 | 9/1975 | Dapcich | 128/400 |
| 4,139,009 | 2/1979 | Gonzalez, Jr. | 128/400 |
| 4,149,541 | 4/1979 | Gammons et al. | 128/400 |
| 4,335,726 | 6/1982 | Kolstedt | 128/400 |
| 4,376,437 | 4/1983 | Sundheim et al. | 128/82.1 |
| 4,474,538 | 10/1989 | Schmid-Schombein et al. | 604/4 |
| 4,739,767 | 5/1987 | Lahr | 128/400 |

FOREIGN PATENT DOCUMENTS 3304697 12/1983 Fed. Rep. of Germany ...... 128/402

OTHER PUBLICATIONS

Resume * of A Seminar on Cryotherapy—May 29-30, 1985 Anaheim, California (3 pages).
Peripheral Edema: Pathophysiology, Evaluation and Management—1987 APTA (8 pages).
ICE Down Cold Therapy Pack!I.C.E. Down Corp., Del Mar, California (2 pages).
Miscellaneous publication "Cryopac" boot (2 pages).
ARTU by Universal, Ankle Treatment Emerges from the Ice Age, Kidde, Inc., Cedar Rapids, Iowa (1 page).
The Air-Stirrup Ankle Brace, Protected Function, Aircast Incorporated, Summit, New Jersey (1 page).
3A Bandage for Knee Joint, ipos USA, Niagara Falls, New York (1 page).
With Little or No Motion, The Compression Knee Dressing (1 page).
Genutrain Active Knee Support, Bauerfeind Therapeutic Aids (1 page).
Cryotherapy and Ankle Sprains, Aircast Inc. (1 page).
Reduction of Edema. Extremity Pumps, Intermittent Compression Unit (1 page).
Products for Physical Medicine (1 page).
Rehabilitation of the Amputee (1 page).

(List continued on next page.)

Primary Examiner—Mark S. Graham
Attorney, Agent, or Firm—Kennedy & Kennedy

[57] ABSTRACT

A cryotheraputic apparatus is disclosed for treating an injury with a cold compress system that has a flexible application bag coupled with a cold liquid supply container via a flexible tube. The flexible application bag is secured about a body member with the bag in contact with the area of injury. The supply container is elevated above the bag so that cold liquid gravitates from the supply container into the application bag causing it to fill and to apply cold and pressure to the area of injury. The height of the supply container above the application bag is adjusted to establish the desired pressure exerted by the application bag upon injury.

14 Claims, 2 Drawing Sheets

OTHER PUBLICATIONS

Our Braces Ar Filled with More Than Just Air, Gelcast Ankle Brace (1 page).
Compact Combination Hot & Cold Compress Therapy Pack, Compac (1 page).
Flowtron Air, Ventilated Compression Systgem, Huntleigh Technology, Inc., Manajapan, New Jersey (2 pages).
Cold Compression Device (4 pages).
Cryotherapy in Seconds, Cryomed Corporation, Princeton, New Jersey (1 page).
Innovations The Cryopac, reprinted from May 1984 edition of Journal of Medical Services, Solana Beach, Calif. (1 page).
Resurgens, The Clinic for Reconstructive Orthopaedic Surgery, John C. Garrett, M.D., Atlanta, Ga. (1 page).

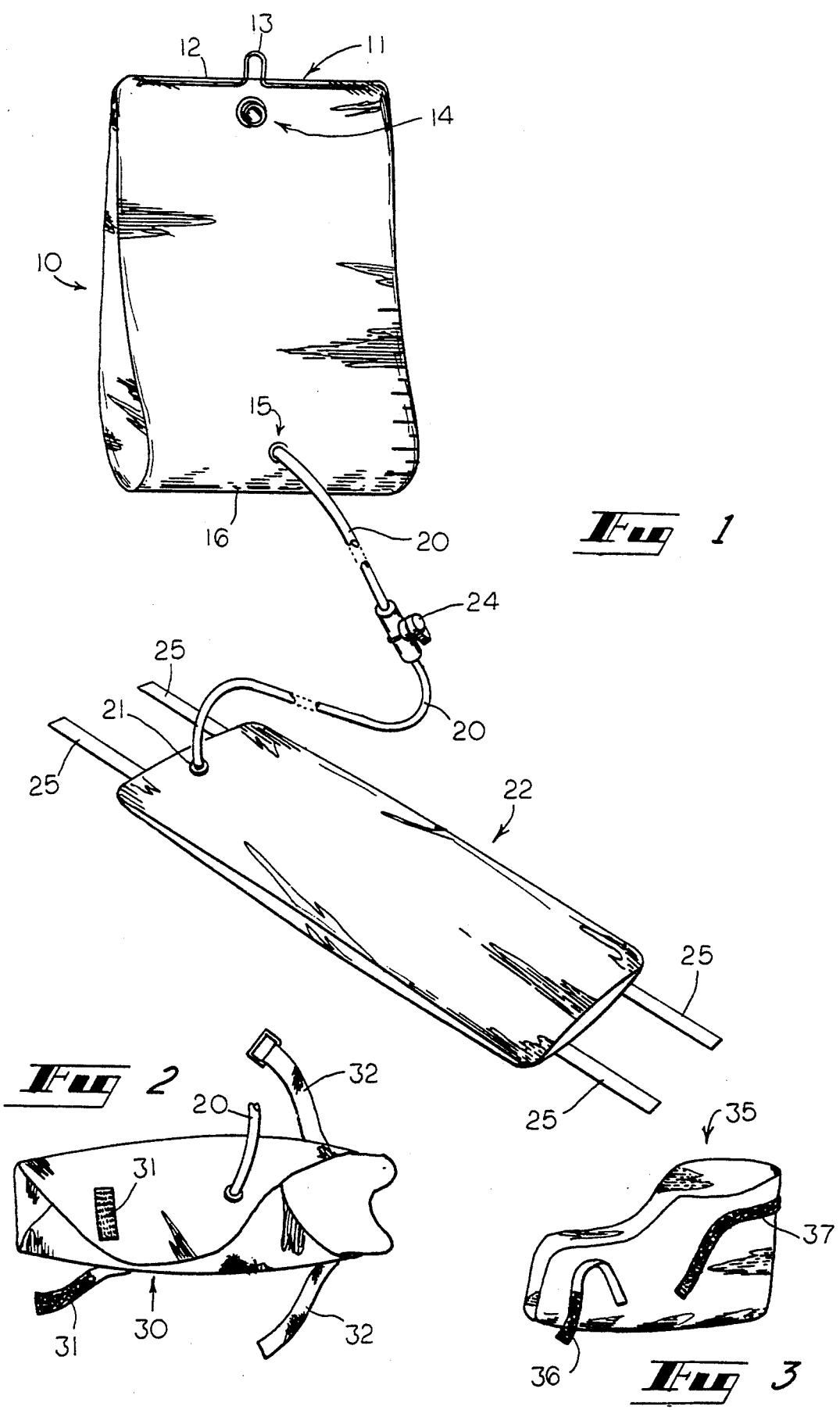

COLD COMPRESS SYSTEM

REFERENCE TO RELATED APPLICATION

This is a continuation of application Ser. No. 408,761 filed Sep. 18, 1989, now abandoned which is a continuation of application Ser. No. 294,428 filed Jan. 9, 1989, now abandoned, which was a division of application Ser. No. 172,578 filed Mar. 24, 1988, also now abandoned.

TECHNICAL FIELD

This invention relates to devices and procedures for use in applying cold and compression to body injuries such as trauma induced and postoperative edema.

BACKGROUND OF THE INVENTION

The use of cold therapy, now termed cryotherapy, is ancient. Indeed, Hippocrates is reported to have noted in 400 B.C. that the application of cold to injuries tends to decrease swelling and to reduce pain by producing numbness. The topical application of pressure to injuries is also well known as a cryotheraputic technique. Particularly in sports medicine, today cryotheraputic procedures are commonly used to reduce edema and tissue damage.

Cryotherapy is also practiced as a postoperative procedure in hospitals with the use of electrically powered apparatuses that create compression and which circulate cold fluids. Outside of institutions such as hospitals, however, the use of electrically powered machines is often impractical or not feasible at all as where no source of electric power is available. Also, where long term treatment is needed for ambulatory patients the coupling of such equipment to the patients as they move about is cumbersome. For the foregoing reasons cold compresses of simple construction have been devised for applying cryotherapy in home and outdoor environments.

Ice packs and bandages have provided the simplest forms of cold compresses. More sophisticated compresses have included reusable cold packs designed to be wrapped around body members such as that known as The Ice Down sold by I.C.E. Down Corporation of Delmar, Calif. Exemplary of the more advanced compression only type products is that known as the Air-Stirrup ankle brace which permits normal flexion to reduce swelling. Other devices have utilized small bottles of pressurized refrigerants for introduction into specially designed boots or the like to provide both a chemical cold pack as well as some degree of compression. A cold compress sold under the name Compac has also been recently marketed as an alternate to ice bags. It is designed to be stored in a refrigerator for later use by being molded about an injury.

Though small cold compresses are seen now to have been developed that provide improvements over simple ice bags and the like, they have not been capable of providing substantial pressure. Compression devices have essentially remained in the domain of the larger type apparatuses that are connected to electrically powered air compressors. Thus, were a relatively small cold compress system to be devised by which both cold and compression could be applied in a substantial and yet easy manner, a distinct advance in the art would be achieved. It is to the provision of such therefore that the present invention is primarily directed.

SUMMARY OF THE INVENTION

In one form of the invention a cold compress system comprises a flexible application pack adapted to be wrapped about an injured body member and which bears fastening means for holding the application bag in place. A cold water supply container is provided from which a flexible tube extends to the application pack to provide fluid communication therebetween. The system also includes valve means for controlling the flow of water between the application pack and supply container.

In a another form of the invention, a cold compress system comprises a reservoir into which a cold liquid may be introduced, an inflatable bag, and fastening means for holding the inflatable bag in a position wrapped securely about an injured body member as the bag is inflated. The system also has means for transferring cold liquid between the reservoir and the bag while the bag remains wrapped securely about the body member. Means are also provided for controlling the transfer of cold liquid between the reservoir and the bag.

A cryotheraputic procedure is provided for treating an injury. In accordance with the procedure an inflatable bag is wrapped about the injury and secured in place so that bag inflation and deflation, caused by infusion and expulsion of a liquid into and out of the bag, alters the pressure applied by the bag to the injury. A cold liquid is then introduced into the bag from a reservoir elevated above the bag until the bag is substantially fully inflated in its secured configuration.

In yet another form of the invention a cryotheraputic procedure is provided for treating an injury with a cold compress system of the type that has a flexible application bag coupled with a cold liquid supply container via a flexible tube. The procedure comprises the steps of securing the flexible application bag about a body member with the bag in contact with the injury and elevating the supply container above the bag whereby cold liquid gravitates from the supply container into the application bag. This action causes the bag to fill and to apply cold and pressure to the area of injury. The height of the supply container is adjusted above the application bag to establish the desired pressure exerted by the application bag upon the injury.

BRIEF DESCRIPTION OF THE DRAWINGS

FIG. 1 is a perspective view of a cold compress system embodying principles of the invention which may be utilized in practicing a cryotheraputic procedure of the invention.

FIG. 2 is a top view of an application pack in an alternative form configured into the shape of a boot.

FIG. 3 is a perspective view of an application pack or bag of another boot-shaped configuration.

DETAILED DESCRIPTION

Figure 4:
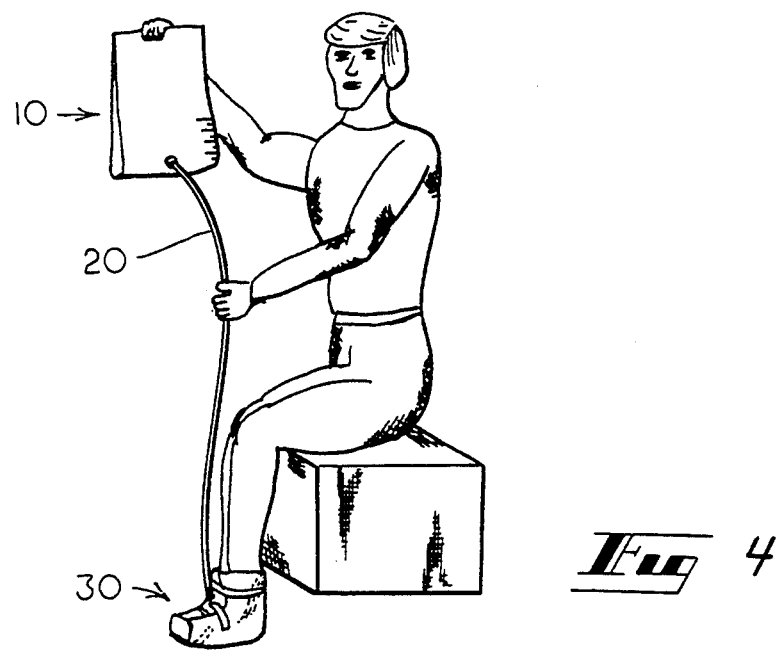
FIG. 4 illustrates a person performing the inventive procedure with the cold compress system while seated.

With reference next to the drawing, there is shown in FIG. 1 a cold compress system which comprises a flexible supply container or reservoir 10 that has a top end 11 that is heat sealed about a wire 12. The wire is formed with a hook 13 for use in hanging the reservoir from an ancillary support. The container 10 is also provided with a port 14 located above its open upper end 11, and which is here shown temporarily closed by a plug, and an outlet 15 located adjacent its bottom end 16.

An elongated, flexible tube 20 extends from the outlet 15 to an inlet 21 of a flexible application pack or bag 22 of generally rectangular configuration. A hand operable flow control valve 24 is provided in the tube 20 for use in controlling the flow of liquid between the reservoir and the application pack. The pack 22 has straps 25 that bear releasibly interlockable masses of fibers such as Velcro.

In preparation for use, the valve 24 is turned to its off position and ice water, with or without a supply of ice cubes, is poured into the reservoir 10 through the port 14. The flexible application pack 22 is then wrapped about an area of injury such as a body limb like a leg or an arm. With the application bag in its deflated configuration wrapped snugly about the limb, it is secured in place with the Velcro bearing straps 25 placed one upon the other in mating engagement.

Next the reservoir 10 is elevated above the now secured application bag and the valve 24 opened whereupon cold water flows down the reservoir and into the application bag. As this occurs the application bag expands and inflates until it is constrained from further significant inflation by the straps 25. As the bag inflates in its constrained state, it commences to apply pressure and cold to the injured body limb. Once the bag has reached its expansion limits imposed by the fastening of the straps 25 this pressure is adjusted by adjusting the height or elevation of the reservoir, with some cold water remaining in it, above the application bag.

Figure 5:
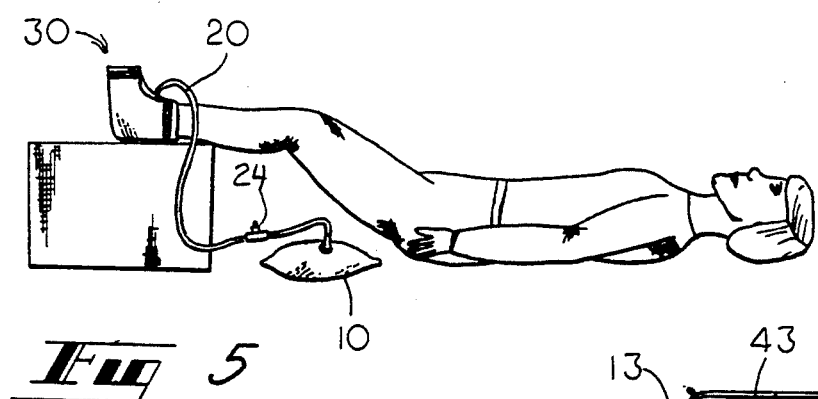
FIG. 5 illustrates a person performing the inventive procedure with the cold compress system while lying down.
Figure 6:
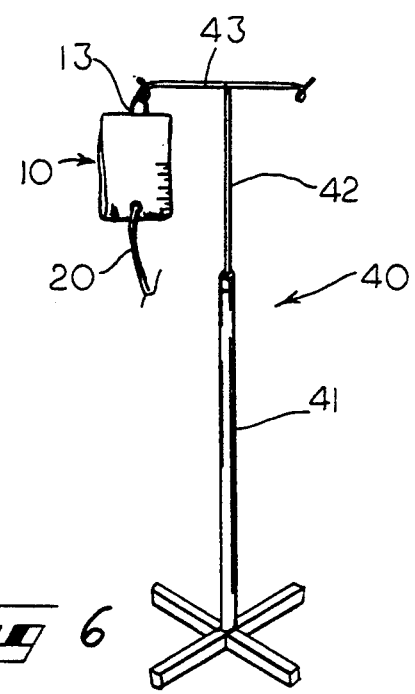
FIG. 6 is a perspective view of an I.V. stand supporting a reservoir component of the cold compress system.

A person using the cold compress system just described may, for example, sit while holding the reservoir bag 10 above himself as illustrated in FIG. 4. With valve 24 open the pressure exerted by the boot-shaped application bag or pack here, which is shown in more detail in FIG. 2, is established by the height at which the person holds the reservoir 10. In other words, if the pressure is too great he simply lowers the bag. Conversely, to increase the pressure he elevates the bag. He may continue to hold the bag at a desired elevation and pressure or he may close valve 24 so that the elevation of the reservoir then ceases to effect the pressure applied by the application bag. This enables him, for example, to lie down with his foot propped up as shown in FIG. 5 and with the reservoir laid on the ground or floor. Alternatively, the reservoir 10 may be suspended as from a stand 40 as shown in FIG. 6. In this case, the stand is a conventional I.V. stand that has a height adjustable member 42 that projects out of a tube base 41. The bag 10 is suspended from a hanger rod 43 mounted atop the member 42.

To terminate the therapy the straps 25 may be simply pulled apart and the application bag unwrapped from about the injury. This may be done without any operation of the valve or movement of the reservoir bag. Of course, the pressure may be more gradually decreased by lowering the reservoir bag with the valve 24 opened thereby causing the pressure applied by the bag to decrease. Even a reverse flow of cold water may occur from the application bag back to the reservoir. In any event it is seen that the system is essentially a closed system although the top of the reservoir bag may be opened to receive ice cubes and cold water, or other cold liquid.

In FIG. 2 an application pack 30 is shown in a configuration that differs from the configuration of the pack 22 illustrated in FIG. 1. The application pack here is shaped to be wrapped about a foot and then secured in place by overlapping two mating strips of Velcro 31 and by buckling straps 32 about an ankle. Thus, the application bag is formable into the configuration of a boot with end portions overlapping one another and held together by the Velcro strips and the ankle strap. The boot-shaped application pack 30 here is the only difference in the cold compress system illustrated in FIG. 1 and is placeable in the same manner in fluid communication with a reservoir by means of the flexible tube 20.

In FIG. 3, an application pack 35 is shown of another configuration but still in the general shape of a boot. In this embodiment only an insubstantial amount of overlay may occur in wrapping the pack about a foot since the application bag is semi-rigidly shaped into an open-top boot. Velcro bearing straps 36 are provided for the toe end while Velcro bearing straps 37 are provided for adapting around the ankle portion of the person in securing the heel portion of the pack. Cold compress systems of the types just described are capable of applying compressive forces of between 0–130 mm of Hg. Filled with ice water the bag typically applies a temperature of approximately 36°–38° F. to an area of injury. Compression has been found to be achievable as follows:

| HEIGHT OF TOP BAG ABOVE BOTTOM BAG | mm Hg Pressure | | |
| --- | --- | --- | --- |
| | FOOT | ANKLE | KNEE |
| 1 foot | 22 | 24 | 26 |
| 2 feet | 45 | 46 | 48 |
| 3 feet | 68 | 66 | 66 |
| 4 feet | 90 | 87 | 88 |
| 5 feet | 114 | 110 | 110 |
| 6 feet | 134 | 131 | 130 |

It thus is seen that a cold compress system and cryotheraputic procedure is now provided that overcomes limitations of those of the prior art. It should be understood, however, that many modification, additions and deletions may be made to the specific embodiments illustrated without departure from the spirit and scope of the invention as set forth in the following claims.

I claim:

1. A cold compress system comprising a flexible inelastic application pack adapted to be wrapped about an injured body member and bearing fastening means for holding the application wrapped securely about the body member; a cold water supply container elevated above said application pack from which cold water may be gravity fed to said application pack; a flexible tube extending between said application pack and said supply container to provide fluid communication therebetween; and valve means for controlling the flow of water between said application pack and said supply container.

2. The cold compress system of claim 1 wherein said flexible application pack is of generally rectangular configuration.

3. The cold compress system of claim 1 wherein said application pack is configurable into the general shape of a boot.

4. The cold compress system of claim 1 wherein said application pack is made of plastic.

5. The cold compress system of claim 1 wherein said fastening means comprises strips of releasibly interlockable fibrous materials.

6. The cold compress system of claim 1 wherein said cold water supply container is a flexible supply bag.

7. The cold compress system of claim 1 further comprising a supply of cold water in said supply container at ambient pressure.

8. A cold compress system comprising, in combination, a reservoir into which a cold liquid may be introduced and from which cold liquid may be freely drained; an inflatable inelastic bag; fastening means for holding said inflatable bag in a position wrapped securely about an injured body member as it inflates below said reservoir; means for transferring cold liquid between said reservoir and said bag while wrapped securely about the body member; and means for controlling the transfer of cold liquid between said reservoir and said bag.

9. The cold compress system of claim 8 wherein said inflatable bag is of generally rectangular configuration.

10. The cold compress system of claim 8 wherein said inflatable bag is configurable into the shape of a boot.

11. The cold compress system of claim 8 further comprising a supply of cold liquid in said reservoir at ambient pressure.

12. The cold compress system of claim 1 further comprising a supply of cold liquid in said supply container at ambient pressure.

13. The cold compress system of claim 1 further comprising means for supporting said cold water supply container above said application pack whereby the desired levels of pressure exerted by the application pack upon the body member may be controlled by the valve means.

14. The cold compress system of claim 8 further comprising support means for supporting said reservoir above said bag with said bag held by said fastening means in a position wrapped about the injured body member whereby control means may establish desired levels of pressure exerted by said bag upon the body member.

* * * * *